United States Patent
Burckhardt et al.

(10) Patent No.: US 10,246,545 B2
(45) Date of Patent: *Apr. 2, 2019

(54) BISMUTH-CONTAINING CATALYST FOR POLYURETHANE COMPOSITIONS

(71) Applicant: SIKA TECHNOLOGY AG, Baar (CH)

(72) Inventors: Urs Burckhardt, Zurich (CH); Rita Cannas, Dubendorf (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/359,666

(22) PCT Filed: Dec. 12, 2012

(86) PCT No.: PCT/EP2012/075205
§ 371 (c)(1),
(2) Date: May 21, 2014

(87) PCT Pub. No.: WO2013/087682
PCT Pub. Date: Jun. 20, 2013

(65) Prior Publication Data
US 2014/0343226 A1 Nov. 20, 2014

(30) Foreign Application Priority Data
Dec. 12, 2011 (EP) .................................. 11193045

(51) Int. Cl.
| | |
|---|---|
| *C07C 235/74* | (2006.01) |
| *C07F 9/94* | (2006.01) |
| *C08G 18/22* | (2006.01) |
| *C08G 18/48* | (2006.01) |
| *C08G 18/76* | (2006.01) |
| *C09D 175/08* | (2006.01) |
| *C09J 175/08* | (2006.01) |

(52) U.S. Cl.
CPC .......... *C08G 18/227* (2013.01); *C07C 235/74* (2013.01); *C07F 9/94* (2013.01); *C08G 18/4812* (2013.01); *C08G 18/4829* (2013.01); *C08G 18/7671* (2013.01); *C09D 175/08* (2013.01); *C09J 175/08* (2013.01); *C08G 2190/00* (2013.01)

(58) Field of Classification Search
CPC .............. C08G 18/227; C08G 18/4829; C08G 18/7671; C08G 18/4812; C08G 2190/00; C07C 235/74; C07F 9/94; C09D 175/08; C09J 175/08

See application file for complete search history.

(56) References Cited

U.S. PATENT DOCUMENTS

| 4,584,362 A | 4/1986 | Leckart et al. |
| 5,719,229 A | 2/1998 | Pantone et al. |
| 8,299,201 B2 | 10/2012 | Burckhardt et al. |
| 2014/0303321 A1* | 10/2014 | Burckhardt ............... C07F 3/06 524/871 |

FOREIGN PATENT DOCUMENTS

| EP | 1 408 062 A1 | 4/2004 |
| JP | A-2005-68402 | 3/2005 |
| WO | WO 2004/033519 A1 | 4/2004 |
| WO | WO 2007/003966 * | 1/2007 |
| WO | WO 2009/050115 A1 | 4/2009 |

OTHER PUBLICATIONS

Inagawa et al., "Two-Component Polyurethane System Sealing Materials with Long Pot Life," Database CA [Online], Chemical Abstracts Service, Columbus, Ohio, US, 2004, XP002670528.
International Search Report issued in International Patent Application No. PCT/EP2012/075205 dated Jan. 30, 2013.
International Preliminary Report on Patentability issued in International Patent Application No. PCT/EP2012/075205 dated Jun. 17, 2014.
Apr. 18, 2016 Office Action issued in Chinese Patent Application No. 201280060790.1.
Oct. 14, 2016 Office Action issued in Chinese Application No. 201280060790.1.
Jul. 26, 2016 Office Action issued in Japanese Patent Application No. 2014-546476.
Nov. 16, 2016 Office Action issued in Russian Patent Application No. 2014118879/04.
Jul. 5, 2017 Office Action issued in Chinese Application No. 201280060790.1.

* cited by examiner

*Primary Examiner* — Patrick D Niland
(74) *Attorney, Agent, or Firm* — Oliff PLC

(57) ABSTRACT

Invention relates to bismuth-containing catalysts, obtainable by reacting at least one bismuth(III) salt or bismuth(III) complex with at least one 1,3-ketoamide with the formula (I). Such complex compounds are suited in particular as catalysts for one- and two-component polyurethane compositions. The invention further relates to two-component polyurethane compositions, including at least one polyisocyanate as the first component, at least one polyol as the second component, and at least one such bismuth-containing catalyst. The invention further relates one-component polyurethane compositions, including at least one polyurethane prepolymer having isocyanate groups, produced from at least one polyisocyanate with at least one polyol, and one such bismuth-containing catalyst. The invention also relates to various uses of the aforementioned polyurethane compositions.

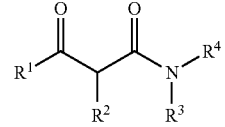

(I)

16 Claims, No Drawings

BISMUTH-CONTAINING CATALYST FOR POLYURETHANE COMPOSITIONS

TECHNICAL FIELD

The present invention relates to the field of polyurethane compositions and to catalysts for polyurethane compositions.

PRIOR ART

Polyurethane compositions have been known for quite some time and are employed in many areas. Traditionally, the expert community distinguishes between one-component and two-component polyurethane compositions. One-component polyurethane compositions cure on exposure to moisture. Two-component polyurethane compositions contain a curing agent as the second component, which essentially comprises polyamines and/or polyols. In both instances, isocyanate group-containing compounds or prepolymers are employed.

To accelerate the curing process, catalysts are admixed. While a plurality of polyurethane catalysts are known, the majority of them are not particularly selective with respect to the urethanization reaction, which is to say the reaction of alcohol OH groups with isocyanate groups, but generally also catalyze other reactions of the isocyanate group, such as allophanate and biuret formation or cyclotrimerization. In particular, the urethanization reaction typically competes with the reaction of the isocyanate groups with water, which results in urea groups with production of gaseous carbon dioxide. This side reaction interferes with many polyurethane compositions, in particular in the use thereof as adhesives and sealants, as coatings or casting resins, since during curing it causes the formation of bubbles, and thus poor dimensional stability, less adhesion, lower mechanical strength, unsatisfactory aesthetics and poorly reproducible results. The water responsible for the formation of bubbles either stems from the residual water content of the constituents of the composition, in particular the polyols and the fillers, which are generally moist even after drying processes and have a typical residual water content of 0.01 to 0.5% by weight, or from the ambient moisture, which penetrates into the composition by diffusion from the air or from the substrates, which occurs in particular in the case of high humidity, porous substrates and/or hydrophilic polyols, such as the polyether polyols frequently employed in practice. In particular the amine catalysts used extensively in practical applications, such as tertiary amines, and tin catalysts, such as dialkyl tin carboxylates, often result in pronounced bubble formation. The residual water content of the polyurethane composition additionally causes catalysts that are sensitive to hydrolysis, such as bismuth carboxylates, to become deactivated if the composition is kept for an extended period prior to use (storage), which adversely affects the curing speed and the mechanical properties. Moreover, the resistance of the cured composition under thermal load is insufficient with some known catalysts, such as dialkyl tin carboxylates, the catalyst causing a decrease in the molecular weight, which is to say depolymerization, with loss of mechanical strength. Moreover, many of the known catalysts are solid at room temperature and poorly soluble in the polyurethane starting materials or the plasticizers, so that organic solvents must be used for their application in compositions that cure at room temperature. Finally, many of the known catalysts, in particular those based on heavy metal compounds, raise toxicological concern.

The use of bismuth compounds as catalysts for curable compounds, such as polyurethane compositions, is known. For example, U.S. Pat. No. 4,584,362 describes the use of bismuth(III) tricarboxylates, such as bismuth-2-ethylhexanoate or bismuth neodecanoate. While such bismuth (III) tricarboxylates are characterized by very high catalytic activity with good selectivity with respect to the urethanization reaction, and additionally do not raise high toxicological concern, they are extremely sensitive to moisture and thus become rapidly deactivated during storage. While according to WO 2004/033519 and U.S. Pat. No. 5,719,229 it was attempted to stabilize bismuth(III) tricarboxylates by way of ligands, such as quinolines, carboxylic acids or diketones, and/or to increase the pot life of the polyurethane composition, the ligands used in the process do not result in sufficient stabilization of the bismuth(III) tricarboxylate or drastically reduce the catalytic activity thereof. In addition, the use of 8-hydroxyquinoline results in worse solubility of the catalyst, which may cause precipitation and necessitate the use of organic solvents. Moreover, significant discoloration of the catalyst and of the cured polyurethane compositions occurs, which is particularly pronounced under the effect of light.

WO 2009/050115 discloses organometallic catalysts, which are suitable for polyaddition or polycondensation reactions. Examples that are listed include bismuth(III) phenyl oxoacetate, bismuth(III) benzoyl benzoate and tris-(4-benzoyl-benzyloxy)-bismuth. Catalysts for polyurethane compositions are also known from JP-A-2005-068402.

DESCRIPTION OF THE INVENTION

It is the object of the present invention to overcome the above-described disadvantages of the prior art. In particular, it is the object of the present invention to provide a catalyst that results in an improvement of the following properties and/or in a balanced proportion of the same.

The catalyst is to be characterized by high catalytic activity and selectivity with regard to the urethanization reactions, which is to say the reaction of alcohol OH groups with isocyanate groups, and thereby enable a rapid synthesis, which has the lowest possible interference from moisture, of a mechanically superior polyurethane polymer from polyfunctional alcohols (polyols) and polyisocyanates In addition, the catalyst is to have sufficient hydrolysis resistance so as to remain intact under customary storage conditions, which is to say at room temperature or at slightly elevated temperatures, over several months in a residual water-containing polyol composition without any significant loss of activity. Moreover, the catalyst is to reduce the thermal resistance of the cured polyurethane polymer as little as possible. Furthermore, the catalyst is to be liquid at room temperature or at slightly elevated temperatures and/or to be easily soluble in the polyurethane starting materials or in the plasticizers, so that it is easy to employ in solvent-free systems that cure at room temperature. Finally, the catalyst is to have as low a toxicity as possible.

mesomeric structures, such as the resonance structures described hereafter. All possible resonance structures of the ligand L with the formula (I) are regarded to be equivalent within the context of the present invention.

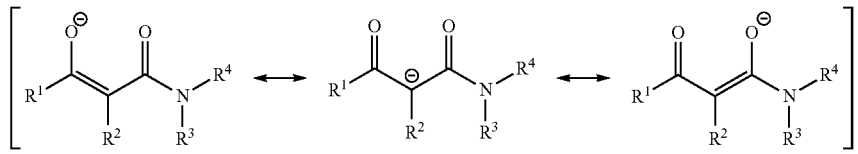

In particular, the catalyst is to have good thermal and hydrolytic stability, thus not hydrolyzing quickly in a residual water-containing polyol, and therefore to maintain the catalytic activity even with extended storage, and it is to be liquid at room temperature and/or have good solubility in plasticizers or polyols, so as to be easy to employ in systems that cure at room temperature, without the use of volatile organic solvents (VOCs).

Finally, the catalyst is to be substantially colorless and should not become discolored even under the effect of light, so as to allow use thereof also in unpigmented or light-colored products without impairment.

Surprisingly, a bismuth-containing catalyst according to claim 1 having the desired properties has now been found. This bismuth-containing catalyst can be obtained by reacting at least one bismuth(III) salt or bismuth(III) complex with at least one 1,3-ketoamide with the formula (I),

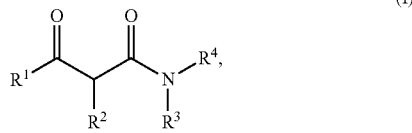

where $R^1$ and $R^2$ independently of one another are a hydrogen group, a monovalent saturated or unsaturated hydrocarbon group having 1 to 10 carbon atoms, or together are a bivalent alkylene group having 3 to 6 carbon atoms, and $R^3$ and $R^4$ independently of one another are a hydrogen group, a monovalent saturated hydrocarbon group, which optionally includes heteroatoms, having 1 to 12 carbon atoms, or together are a bivalent alkylene group, which optionally includes heteroatoms, having 3 to 6 carbon atoms.

The stoichiometric ratio between the bismuth(III) salt or the bismuth(III) complex and the 1,3-ketoamide with the formula (I) preferably ranges between approximately 1:0.5 and 1:20, particularly preferably between 1:1 and 1:10, and most preferably between 1:3 and 1:6. This results in the advantage that the catalyst exhibits good stability to hydrolysis and also high catalytic activity.

It is assumed that a complexation reaction takes place between the bismuth(III) salt or the bismuth(III) complex and the 1,3-ketoamide with the formula (I) with formation of bismuth(III)-1,3-ketoamide complexes, in which at least one 1,3-ketoamide with the formula (I) is formally present as a ligand in a singly negatively charged form.

Since the negative charge is delocalized via the 1,3-ketoamide structure, the ligand can be mapped in various In formula (I), $R^1$ and $R^2$ independently of one another are a hydrogen group, a monovalent saturated or unsaturated hydrocarbon group having 1 to 10 carbon atoms, or together are a bivalent alkylene group having 3 to 6 carbon atoms.

The monovalent saturated hydrocarbon group having 1 to 10 carbon atoms is preferably an alkyl group having 1 to 4 carbon atoms, in particular a methyl or butyl group. These have the advantage that the complex compound thus tends to be liquid or easily soluble. The monovalent unsaturated hydrocarbon group is preferably also an aryl group, and more particularly a phenyl group.

$R^2$ is particularly preferably a hydrogen group, since the complex compound thus tends to be particularly stable.

A bivalent alkylene group having 3 to 6 carbon atoms shall be understood to mean a group with the formula —$(CH_2)_n$—, where n is 3 to 6.

$R^1$ and $R^2$ together preferably form a bivalent alkylene group having 3 to 4 carbon atoms, and more particularly having 3 carbon atoms.

$R^3$ and $R^4$ independently of one another are a hydrogen group, a monovalent saturated hydrocarbon group, which optionally includes heteroatoms, having 1 to 12 carbon atoms, or together are a bivalent alkylene group, which optionally includes heteroatoms, having 3 to 6 carbon atoms.

The monovalent saturated hydrocarbon group having 1 to 12 carbon atoms is preferably an alkyl group having 1 to 8 carbon atoms, and particularly preferably a methyl, an ethyl, a propyl, an isopropyl, a butyl, an isobutyl, a hexyl, a 2-methyl-pentyl, an octyl or a 2-ethyl-hexyl group. This had the advantage that the complex compound thus tends to be liquid or easily soluble. The monovalent saturated hydrocarbon group having 1 to 12 carbon atoms can preferably also be a cycloalkyl group having 5 to 6 carbon atoms, and particularly preferably 6 carbon atoms. The monovalent saturated hydrocarbon group including heteroatoms is preferably a hydroxyalkyl group having 1 to 4 carbon atoms, and particularly preferably a 2-hydroxyethyl or 2-hydroxypropyl group. This has the advantage that the complex compound thus tends to be liquid or easily soluble and the ligand can be covalently incorporated into the polymer during curing. An alkyl ether group having 1 to 4 carbon atoms is also preferred, a 2-methoxyethyl or a 2-(2-methoxy)ethoxyethyl group being particularly preferred, since the complex compound thus tends to be liquid or easily soluble.

$R^3$, together with $R^4$, can also form a bivalent alkylene group with the formula —$(CH_2)_n$—X—$(CH_2)_n$— with X=O, NR, where R is a monovalent alkyl group having 1 to 4 carbon atoms, or S and n=2 to 4. Particularly preferably n=2 and X=O or NR.

The selection of the preferred groups in the ligands L with the formula (I) is preferably based on the aspect that the corresponding 1,3-ketoamides, which are used as starting materials for producing the bismuth-containing catalyst according to the invention, are easy to produce and/or commercially available and thus inexpensive.

The following bismuth-containing catalysts (1) to (8) having ligands L with the formula (I) are particularly preferred, where $R^1$ to $R^4$ have the meanings indicated in the table.

| | $R^1$ | $R^2$ | $R^3$ | $R^4$ |
|---|---|---|---|---|
| (1) | Alkyl group having 1 to 4 carbon atoms | Hydrogen group | Alkyl group having 1 to 8 carbon atoms | Alkyl group having 1 to 8 carbon atoms |
| (2) | Phenyl group | Hydrogen group | Alkyl group having 1 to 8 carbon atoms | Alkyl group having 1 to 8 carbon atoms |
| (3) | Alkyl group having 1 to 4 carbon atoms | Hydrogen group | Alkylether group having 1 to 4 carbon atoms | Alkylether group having 1 to 4 carbon atoms |
| (4) | Alkylene group having 3 to 6 carbon atoms | | | Alkyl group having 1 to 8 carbon atoms |
| (5) | Alkyl group having 1 to 4 carbon atoms | Hydrogen group | Alkylene group with the formula —(CH$_2$)$_n$—X—(CH$_2$)$_n$—with X = O or NR and n = 2 | |
| (6) | Alkyl group having 1 to 4 carbon atoms | Hydrogen group | Cycloalkyl group having 5 to 6 carbon atoms | Alkyl group having 1 to 8 carbon atoms |
| (7) | Alkyl group having 1 to 4 carbon atoms | Hydrogen group | Alkyl group having 1 to 8 carbon atoms | Cycloalkyl group having 5 to 6 carbon atoms |
| (8) | Phenyl group | Hydrogen group | Alkylene group with the formula (—CH$_2$)$_n$—X—(CH$_2$)$_n$—with X = O or NR and n = 2 | |

The bismuth-containing catalyst according to the invention preferably has the formula Bi(L)$_x$(Y)$_{3-x}$, in which x is 1, 2 or 3, y is a singly negative ligand, and L is a ligand with the formula (I).

The bismuth-containing catalyst is produced by reacting at least one bismuth(III) salt or bismuth(III) complex with at least one 1,3-ketoamide with the formula (I),

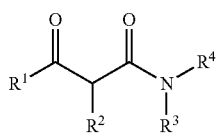

(I)

where $R^1$, $R^2$, $R^3$ and $R^4$ are as defined above. The use of a bismuth(III) carboxylate, in particular bismuth(III) neodecanoate or bismuth(III)-2-ethylhexanoate, is preferred.

The at least one bismuth(III) salt or the at least one bismuth(III) complex and the at least one 1,3-ketoamide with the formula (I) are mixed, and the mixture is heated to a temperature of 50 to 130° C., preferably approximately 80° C., preferably while stirring for 1 to 24 hours, preferably approximately 2 hours. The reaction mixture is thereafter preferably cooled, preferably to room temperature.

The bismuth-containing catalyst according to the invention can be used as a catalyst for curable compounds, preferably for polyurethane compositions. The bismuth-containing catalyst according to the invention accelerates the curing of curable compounds that include reactive groups capable of cross-linking reactions. The curable compounds can have single-component or multi-component formulations.

The bismuth-containing catalyst according to the invention preferably accelerates the curing of two-component polyurethane compositions, which cross-link with one another and optionally under the effect of moisture via blocked or in particular free isocyanate groups. This accelerates in particular the urethanization reaction, which is to say the reaction of isocyanate groups with alcohol OH groups. The compositions to be cross-linked may also include further reactive groups capable of cross-linking reactions, such as in particular alkoxysilane groups. These are preferably trialkoxysilane groups, as they can be found in silane adhesive promoters, for example.

The bismuth-containing catalyst according to the invention can advantageously be employed as a catalyst in a two-component polyurethane composition. In addition to the bismuth-containing catalyst according to the invention, this composition includes a polyol as the first component and a polyisocyanate as the second component.

The term "two-component" denotes a composition in which the constituents of the same are present in two different components, which are stored in separate containers and which on their own are storage stable in each case.

The two components are not mixed with each other until just prior to or during the application of the composition, whereupon the mixed composition cures, curing in some circumstances only taking place or being completed under the action of moisture and/or an elevated temperature.

Substance names beginning with "poly", such as polyol or polyisocyanate, denote substances that, per molecule, formally comprise two or more of the functional groups occurring in their names.

The term "polyisocyanate" comprises compounds having two or more isocyanate groups, regardless of whether these are monomeric diisocyanates, oligomeric polyisocyanates or polymers comprising isocyanate groups.

A suitable polyisocyanate, for example, is a polyisocyanate in the form of a monomeric diisocyanate or triisocyanate or an oligomer of a monomeric diisocyanate or a derivative of a monomeric diisocyanate.

For example, suitable monomeric diisocyanates or triisocyanates are 1,4-tetramethylene diisocyanate, 2-methylpentamethylene-1,5 diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane-1,3 and -1,4 diisocyanate, 1-methyl-2,4- and -2,6-diisocyanato cyclohexane and any arbitrary mixtures of these isomers, 1-isocyanato-3,3,5-trimethyl-5-isocyanatomethyl cyclohexane (=isophorone diisocyanate or IPDI), perhydro-2,4'- and -4,4'-diphenylmethane diisocyanate (HMDI), 1,4-diisocyanato-2,2,6-trimethylcyclohexane (TMCDI), 1,3- and 1,4-bis-(isocyanatomethyl)-cyclohexane, m- and p-xylylene diisocyanate (m- and p-XDI), m- and p-tetramethyl-1,3- and -1,4-xylylene diisocyanate (m- and p-TMXDI), bis-(1-isocyanato-1-methylethyl)naphthalene, dimer and trimer fatty acid isocyanates, such as 3,6-bis-(9-isocyanatononyl)-4,5-di-(1-heptenyl)cyclohexene (dimeryl diisocyanate), α,α,α',α',α'',α''-hexamethyl-1,3,5-mesitylene triisocyanate, 2,4- and 2,6-toluylene diisocyanate and arbitrary mixtures of these isomers (TDI), 4,4'-, 2,4'- and 2,2'-diphenylmethane diisocyanate and arbitrary mixtures of these isomers (MDI), mixtures made of MDI and MDI homologs (polymeric MDI or PMDI), 1,3- and 1,4-phenylene diisocyanate, 2,3,5,6-tetramethyl-1,4-diisocyanatobenzene, naphthalene-1,5-diisocyanate (NDI), 3,3'-dimethyl-4,4'-diisocyanatodiphenyl (TODI), dianisidine diisocyanate (DADI), 1,3,5-tris-(isocyanatomethyl)benzene, tris-(4-isocyanatophenyl)methane and tris-(4-isocyanatophenyl)thiophosphate.

Preferred polyisocyanates are commercially available diisocyanates. Particularly preferred are HDI, IPDI, TDI and MDI as well as oligomers of diisocyanates and isocyanate group-comprising polyurethane polymers (NCO prepolymers).

For example, the following commercially available polyols, or mixtures thereof, can be used as polyols:

Polyoxyalkylene polyols, also referred to as polyether polyols or oligoetherols, which are polymerization products of ethylene oxide, 1,2-propylene oxide, 1,2- or 2,3-butylene oxide, oxetane, tetrahydrofurane or mixtures thereof, potentially polymerized with the aid of a starter molecule having two or more active hydrogen atoms, such as water, ammonia or compounds comprising multiple OH or NH groups, such as 1,2-ethanedial, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexane dimethanol, bisphenol A, hydrogenated bisphenol A, 1,1,1-trimethylolethane, 1,14-trimethylolpropane, glycerin, aniline, as well as mixtures of the above-mentioned compounds. It is possible to use both polyoxyalkylene polyols that have low levels of unsaturation (as measured according to ASTM D-2849-69 and indicated in milliequivalents unsaturation per gram of polyol (mEq/g)), for example produced with the aid of what are known as double metal cyanide complex catalysts (DMC catalysts), and polyoxyalkylene polyols that have higher levels of unsaturation, for example produced with the aid of anionic catalysts such as NaOH, KOH, CsOH or alkali alcoholates.

Polyoxyalkylene diols or polyoxyalkylene triols, and more particularly polyoxyethylene and polyoxypropylene diols and triols, are particularly suitable. Specifically suited are polyoxyalkylene diols and triols having a level of unsaturation of less than 0.02 mEq/g and a molecular weight ranging from 1,000 to 30,000 g/mol, and polyoxypropylene diols and triols having a molecular weight ranging from 400 to 8,000 g/mol.

So-called ethylene oxide-terminated ("EO-endcapped", ethylene oxide-endcapped)) polyoxypropylene polyols are likewise particularly suitable. The latter are special polyoxypropylene polyoxyethylene polyols, which can be obtained, for example, by further alkoxylating pure polyoxypropylene polyols, in particular polyoxypropylene diols and trials, after the polypropoxylation reaction with ethylene oxide is completed, as a result of which these comprise primary hydroxyl groups.

Polyether polyols grafted with styrene-acrylonitrile or acrylonitrile-methyl methacrylate.

Polyester polyols, also referred to as oligoesterols, produced according to known methods, in particular the polycondensation of hydroxycarboxylic acids or the polycondensation of aliphatic and/or aromatic polycarboxylic acids with dihydric or polyhydric alcohols. Particularly suitable polyester polyols are those which are produced from dihydric to trihydric, in particular dihydric alcohols, such as ethylene glycol, diethylene glycol, propylene glycol, dipropylene glycol, neopentyl glycol, 1,4-butanediol, 1,5-pentanediol, 3-methyl-1,5-hexanediol, 1,6-hexanediol, 1,8-octanediol, 1,10-decanediol, 1,12-dodecanediol, 1,12-hydroxystearyl alcohol, 1,4-cyclohexane dimethanol, dimer fatty acid diol (dimer diol), hydroxypivalinic acid neopentyl glycol ester, glycerin, 1,1,1-trimethylolpropane, or mixtures of the aforementioned alcohols, with organic dicarboxylic or tricarboxylic acids, in particular dicarboxylic acids, or the anhydrides or esters thereof, such as succinic acid, glutaric acid, adipic acid, trimethyl adipic acid, suberic acid, azelaic acid, sebacic acid, dodecanedicarboxylic acid, maleic acid, fumaric acid, dimer fatty acid, phthalic acid, phthalic acid anhydride, isophthalic acid, terephthalic acid, dimethyl terephthalate, hexahydrophthalic acid, trimellitic acid and trimellitic acid anhydride, or mixtures of the aforementioned acids, and polyester polyols made of lactones, such as E caprolactone and starters, such as the aforementioned dihydric and trihydric alcohols.

Polycarbonate polyols, such as those that become available by reacting, for example, the above-mentioned alcohols—used for the synthesis of the polyester polyols—with dialkyl carbonates, diaryl carbonates or phosgene.

Block copolymers which carry at least two hydroxyl groups and which comprise at least two different blocks having a polyether, polyester and/or polycarbonate structure of the type described above, in particular polyether polyester polyols.

Polyacrylate and polymethacrylate polyols.

Polyhydroxy-functional fats and oils, such as natural fats and oils, in particular castor oil; or polyols obtained by chemical modification of natural fats and oils—so-called oleochemical polyols—such as the epoxy polyesters or epoxy polyethers obtained by epoxidation of unsaturated oils and by subsequent ring opening with carboxylic acids or alcohols, or polyols obtained by hydroformylation and hydrogenation of unsaturated oils; or polyols obtained from natural fats and oils by decomposition processes such as alcoholysis or ozonolysis and subsequent chemical cross-linkage, such as by transesterification or dimerization, of the decomposition products thus gained or derivatives thereof. Suitable decomposition products of natural fats and oils are in particular fatty acids and fatty alcohols as well as fatty acid esters, in particular the methyl esters (FAME), which can be derivatized by hydroformylation and hydrogenation to form hydroxyfatty acid esters, for example.

Polyhydrocarbon polyols, also referred to as oligohydrocarbonols, such as polyhydroxy-functional polyolefins, polyisobutylenes, polyisoprenes; polyhydroxy-functional ethylene propylene, ethylene butylene or ethylene propylene diene copolymers; polyhydroxy-functional polymers of dienes, in particular of 1,3-butadiene, which can produced in particular also from anionic polymerization; polyhydroxy-functional copolymers from dienes such as 1,3-butadiene or diene mixtures and vinyl monomers such as styrene, acrylonitrile, vinyl chloride, vinyl acetate, vinyl alcohol, isobutylene and isoprene, for example polyhydroxy-functional acrylonitrile/butadiene copolymers, as they can be produced, for example, from epoxides or amino alcohols and carboxyl-terminated acrylonitrile/butadiene copolymers; and hydrogenated polyhydroxy-functional polymers or copolymers of dienes.

The above-mentioned polyols preferably have an average molecular weight of 250 to 30,000 g/mol, in particular of 400 to 20,000 g/mol, and further preferably have an average OH functionality in the range of 1.6 to 3.

The term "molecular weight" of oligomers or polymers is always understood to mean the number average molecular weight $M_n$.

The use of polyether polyols is particularly preferred, preferably polypropylene polyols and mixed polyethylene polypropylene polyols, and polyester polyols and polycarbonate polyols.

The bismuth-containing catalyst according to the invention is preferably present in the first component, which has the advantage that the storage stability (shelf life) of the polyisocyanate, which is sensitive to catalytically acting compounds, in the second component is not impaired.

The bismuth-containing catalyst according to the invention can be used as a catalyst alone or together with other catalysts, such as bismuth, tin or zirconium compounds or tertiary amines, for example.

The bismuth-containing catalyst according to the invention can optionally comprise further customarily used auxiliary substances and additives, such as pigments, plasticizers or diluents, curing agents, cross-linking agents, chain extenders, further catalysts, adhesive promoters, stabilizers, rheology additives and drying agents, and the like.

The bismuth-containing catalyst according to the invention, when considered in terms of the quantity of elemental bismuth, is preferably present in the two-component polyurethane composition according to the invention in a quantity of 0.0002 to 1% by weight, particularly preferably in a quantity of 0.001 to 0.2% by weight, and most preferably in a quantity of 0.002 to 0.1% by weight, based on the weight of the composition. Excessively high quantities cause the open time or processing time of the composition to be too short, while the use of excessively low quantities has the disadvantage that the composition is poorly catalyzed and thus cures too slowly, incompletely and/or incorrectly. In the two-component polyurethane composition according to the invention, the bismuth-containing catalyst according to the invention accounts for 0.001 to 5, preferably 0.005 to 1, and particularly preferably 0.01 to 0.5 mmol-equivalent bismuth atoms based on 100 g of the composition.

As was already mentioned above, the bismuth-containing catalyst according to the invention is comparatively active and also comparatively selective with regard to the urethanization reaction. For example, the bismuth-containing catalyst according to the invention is characterized by high catalytic activity, even with extended storage. The two-component polyurethane composition generally cures quickly. The selectivity of the bismuth-containing catalyst according to the invention is not adversely affected by the increased activity; curing takes place without the formation of bubbles, even under unfavorable conditions, such as a high temperature, high ambient moisture or a high residual water content of the composition, and with the use of polyols comprising secondary OH groups or hydrophilic polyols. The bismuth-containing catalyst according to the invention is comparatively stable both thermally and hydrolytically, decomposes only slowly even in a polyol having a residual water content, and thus maintains the catalytic activity thereof even with extended storage durations. Nonetheless, the use of the bismuth-containing catalyst according to the invention results in good stability of the cured polyurethane composition under thermal load. Moreover, at room temperature the bismuth-containing catalyst according to the invention is liquid and/or easily soluble in plasticizers or polyols and is thus easy to employ in systems that cure at room temperature, in particular without the use of volatile organic solvents (VOCs). Finally, the bismuth-containing catalyst according to the invention is colorless and also does not become discolored under the effect of light, so that it can also be used in unpigmented or light-colored products without admixing. The polyurethane compositions cured with the bismuth-containing catalyst according to the invention exhibit good thermal resistance, despite their stability to hydrolysis, and do not tend more strongly toward discoloration than those cured with bismuth(III) carboxylates.

The two-component polyurethane composition according to the invention can be employed in many areas, for example as a casting compound, sealant, adhesive, covering, coating, paint, subcoating, rigid foam, flexible foam, molding, elastomer, fiber, film or membrane for building and industrial applications, for example as an electrical potting compound, knifing filler, seam sealant, cavity sealant, joint sealant, assembly adhesive, autobody adhesive, window adhesive, sandwich element adhesive, laminating adhesive, laminate adhesive, packaging adhesive, wood glue, parquet flooring adhesive, anchoring adhesive, floor covering and coating, balcony and roof coating, protective concrete coating, parking garage coating, pipe coating, anti-corrosive coating, textile coating, wood paint, decorative paint, primer, furniture foam, upholstery foam, filter foam, insulating foam, sound insulating foam, sealing foam, packaging foam, autobody foam, pattern plate, damping element, sealing element, tire, roller, bearing, cylinder, conveyor belt, elastic thread, shoe sole, housing, window casement section, implant, cellular rubber and the like.

Preferred fields of application are casting compounds, sealants, adhesives, coverings, coatings, paints, subcoatings, moldings and elastomers for building and industrial applications.

The bismuth-containing catalyst according to the invention can also be used in one-component polyurethane compositions. In addition to the bismuth-containing catalyst according to the invention, these comprise at least one polyurethane prepolymer which have terminal isocyanate groups and are produced from at least one polyisocyanate and at least one polyol. The polyurethane prepolymer is produced in the customary manner, as is described in EP 1 408 062 A1, for example. The polyols employed for the production of the prepolymer are those described in EP 1 408 062 and above. The same applies to the polyisocyanates used for producing the polyurethane prepolymers.

In the one-component polyurethane composition according to the invention, the bismuth-containing catalyst according to the invention accounts for 0.02 to 5, preferably 0.1 to 2.5, and particularly preferably 0.2 to 1 mmol-equivalent bismuth atoms based on 100 g of the composition.

One-component polyurethane compositions comprising a bismuth-containing catalyst according to the invention typically have identical or similar advantages as the above-described two-component polyurethane compositions, in particular comparatively good storage stability and skinning times.

The fields of application of the one-component polyurethane composition according to the invention correspond to those of the applications described above in connection with the two-component polyurethane compositions.

In addition to one-component and two-component polyurethane compositions, the bismuth-containing catalyst according to the invention can also be used as a catalyst or co-catalyst in other curable compounds, such as in epoxy resins, acrylates and silicones.

EXAMPLES

Description of the Measuring Methods

Infrared spectra were measured on an FT-IR 1600 device made by Perkin-Elmer (horizontal ATR measuring unit with ZnSe crystal; measurement window 4000-650 cm$^{-1}$). Liquid samples were applied undiluted as films; solid samples were dissolved in $CH_2Cl_2$. The absorption bands are indicated in wavenumbers (cm$^{-1}$).

$^1$H NMR spectra were measured on a spectrometer of the type Bruker DPX-300 at 300.13 MHz; the chemical shift δ is indicated in ppm relative to tetramethylsilane (TMS). No distinction was made between true and pseudo coupling patterns.

The viscosity was measured on a thermostated Physica MCR 300 cone and plate viscosimeter (cone diameter 20 mm, cone angle 1°, cone tip-plate distance 0.05 mm, shear rate 0.1 to 100 s$^{-1}$).

UV-vis spectra of samples dissolved in dichloromethane (40 mg/l) in 1 cm quartz cuvettes were measured on a spectrometer of the type Varian Cary 50 in the wavelength range of 800 to 200 nm. Indicated are the absorbance maxima $\lambda_{max}$ in nm and, in parentheses, the related molar extinction coefficients ε in l·g$^{-1}$·cm$^{-1}$.

Production of the Polyurethane Catalysts

General Production Protocol A

Commercial bismuth(III) tris(neodecanoate) and a 1,3-ketoamide were mixed in a round-bottomed flask and the mixture was heated to 80° C. while stirring for 2 hours. Thereafter, the reaction mixture was cooled to room temperature.

Example 1: Catalyst Bi1

In accordance with the general production protocol A, 7.75 g Coscat® 83 (bismuth(III) tris(neodecanoate) in neodecanoic acid; 16% Bi; from Erbslöh) and 2.85 g N,N-diethyl-3-oxobutanamide were reacted. This yielded a pale yellow oil.

FT-IR: 2957, 2933, 2873, 1722, 1698, 1636, 1606, 1545, 1462, 1381, 1361, 1313, 1272, 1217, 1162, 1098, 1080, 942, 907, 872, 826, 789.

UV-vis: 258 (0.5). (see Coscat® 83: 267(0.3).)

Example 2: Catalyst Bi2

In accordance with the general production protocol A, 4.29 g Coscat® 83 (16% Bi; from Erbslöh) and 3.11 g N,N-diethyl-3-oxobutanamide were reacted. This yielded a pale yellow oil.

FT-IR: 2958, 2931, 2872, 1722, 1636, 1605, 1460, 1381, 1360, 1313, 1272, 1217, 1148, 1098, 1080, 942, 921, 826, 774, 730.

Example 3: Catalyst Bi3

In accordance with the general production protocol A, 6.62 g NeoBi 200BA (bismuth(III) tris(neodecanoate) in neodecanoic acid; 20% Bi; from Shepherd) and 5.98 g N,N-diethyl-3-oxobutanamide were reacted. This yielded a pale yellow oil.

FT-IR: 2960, 2931, 2874, 1720, 1635, 1593, 1490, 1461, 1390, 1359, 1312, 1272, 1220, 1199, 1148, 1098, 1080, 1007, 942, 919, 826, 774, 728.

Example 4: Catalyst Bi4

In accordance with the general production protocol A, 1.40 g Coscat® 83 (16% Bi; from Erbslöh) and 1.38 g N,N-dibutyl-3-oxobutanamide were reacted. This yielded a pale yellow oil.

FT-IR: 2957, 2930, 2872, 1721, 1635, 1605, 1490, 1461, 1362, 1293, 1226, 1159, 931, 773, 732.

Example 5: Catalyst Bi5

In accordance with the general production protocol A, 2.63 g Coscat® 83 (16% Bi; from Erbslöh) and 3.09 g N,N-dibutyl-3-oxoheptanamide were reacted. This yielded a pale yellow oil.

FT-IR: 2956, 2930, 2872, 1717, 1630, 1607, 1489, 1464, 1378, 1292, 1255, 1222, 1146, 932, 817, 775, 731.

Example 6: Catalyst Bi6

In accordance with the general production protocol A, 4.33 g Coscat® 83 (16% Bi; from Erbslöh) and 3.42 g N,N-bis(2-ethylhexyl)-3-oxobutanamide were reacted. This yielded an almost colorless oil.

FT-IR: 2957, 2927, 2872, 1698, 1632, 1602, 1546, 1461, 1380, 1359, 1232, 1159, 1006, 934, 818, 773, 728.

Example 7: Catalyst Bi7

In accordance with the general production protocol A, 4.16 g Coscat® 83 (16% Bi; from Erbslöh) and 3.51 g N,N-bis(2-ethylhexyl)-2-oxocyclopentane carboxamide were reacted. This yielded a pale yellow oil.

FT-IR: 2957, 2928, 2872, 1740, 1698, 1640, 1606, 1546, 1536, 1460, 1379, 1216, 1149, 1108, 1003, 935, 904, 872, 833, 766, 728.

Example 8: Catalyst Bi8

In accordance with the general production protocol A, 4.53 g Coscat® 83 (16% Bi; from Erbslöh) and 3.00 g N,N-dibutyl-3-oxo-3-phenylpropanamide were reacted. This yielded a light yellow oil.

FT-IR: 2957, 2931, 2871, 1736, 1695, 1599, 1575, 1484, 1466, 1366, 1292, 1215, 1153, 1085, 1000, 942, 907, 874, 817, 764, 716, 688.

Comparison Example: Catalyst Bi9

0.88 g Coscat® 83 (16% Bi; from Erbslöh) and 0.21 g 2,4-pentanedione were mixed in a round-bottomed flask and the mixture was heated to 80° C. while stirring over 2 hours. Thereafter, the reaction mixture was cooled to room temperature. This yielded a colorless oil.

Comparison Example: Catalyst Bi10

1.40 g Coscat® 83 (16% Bi; from Erbslöh) and 0.66 g 2,4-pentanedione were mixed in a round-bottomed flask and the mixture was heated to 80° C. while stirring over 2 hours. Thereafter, the reaction mixture was cooled to room temperature. This yielded a colorless oil.

Comparison Example: Catalyst Bi11

1.10 g Coscat® 83 (16% Bi; from Erbslöh) and 0.34 g ethyl acetoacetate were mixed in a round-bottomed flask and the mixture was heated to 80° C. while stirring over 2 hours. Thereafter, the reaction mixture was cooled to room temperature. This yielded a slightly pink-colored oil.

Comparison Example: Catalyst Bi12

1.20 g Coscat® 83 (16% Bi; from Erbslöh) and 0.73 g ethyl acetoacetate were mixed in a round-bottomed flask and the mixture was heated to 80° C. while stirring over 2 hours. Thereafter, the reaction mixture was cooled to room temperature. This yielded a slightly pink-colored oil.

Comparison Example: Catalyst Bi13

1.25 g Coscat® 83 (16% Bi; from Erbslöh) and a solution of 0.44 g 8-hydroxyquinoline in 3.27 g diisodecyl phthlate were mixed in a round-bottomed flask and the mixture was heated to 80° C. while stirring over 2 hours. Thereafter, the reaction mixture was cooled to room temperature. This yielded a deep-yellow suspension.

Comparison Example: Catalyst Bi14

1.26 g Coscat® 83 (16% Bi; from Erbslöh) and a solution of 0.40 g salicylic acid in 3.49 g diisodecyl phthlate were mixed in a round-bottomed flask and the mixture was heated to 80° C. while stirring over 2 hours. Thereafter, the reaction mixture was cooled to room temperature. This yielded an almost colorless liquid.

Two-Component Polyurethane Compositions

Examples 9 to 10 and Comparison Examples V1 to V5

To produce the first component, a polyether triol (Voranol® CP 4755, from Dow) and a catalyst according to Table 1 were homogeneously mixed in a centrifugal mixer (SpeedMixer™ DAC 150, FlackTek Inc.) for 30 seconds at 3000 rpm for each example. A portion of the freshly prepared first component was then filled into an aluminum tube coated on the inside, the tube was hermetically sealed and stored for 7 days in a circulating air oven at 60° C.

The remaining portion of the freshly prepared first component was mixed for each example in the described manner with a modified diphenylmethane diisocyanate (Desmodur® CD-L, from Bayer), which is liquid at room temperature, as the second component in accordance with Table 1 to form a polyurethane composition.

For each example, the first component, which had been stored for 7 days at 60° C., was likewise mixed with the second component in accordance with Table 1 in the same manner to form a polyurethane composition.

TABLE 1

Two-component polyurethane compositions (quantities in parts by weight).

| Example | 9 | 10 | V1 | V2 | V3 | V4 | V5 |
|---|---|---|---|---|---|---|---|
| First component: | | | | | | | |
| Voranol ® CP 4755 | 50 | 50 | 50 | 50 | 50 | 50 | 50 |
| Catalyst Bi1 | 0.014 | — | — | — | — | — | — |
| Catalyst Bi2 | — | 0.022 | — | — | — | — | — |
| Catalyst Bi9 | — | — | 0.013 | — | — | — | — |
| Catalyst Bi10 | — | — | — | 0.026 | — | — | — |
| Catalyst Bi11 | — | — | — | — | 0.011 | — | — |
| Catalyst Bi13 | — | — | — | — | — | 0.040 | — |
| Coscat ® 83[a] | — | — | — | — | — | — | 0.020 |
| mmol-equiv./100 g[b] | 0.014 | 0.018 | 0.015 | 0.025 | 0.012 | 0.014 | 0.028 |
| Second component: | | | | | | | |
| Desmodur ® CD-L | 5.10 | 5.10 | 5.10 | 5.10 | 5.10 | 5.10 | 5.10 |

[a]Bismuth(III) tris(neodecanoate) in neodecanoic acid (16% Bi, from Erbslöh).
[b]mmol-equivalent bismuth atoms of the catalyst based on 100 g of the composition.

The polyurethane compositions were tested with respect to aspect ratio, color, tack-free time, bubble formation and Shore A hardness, in each case both for the composition comprising the freshly prepared first component and for the composition comprising the first component that had been stored for 7 days at 60° C. Thereafter the mechanical properties were also measured in a tensile test, only for the composition comprising the freshly prepared first component, in particular before and after various storage conditions for accelerated aging of the samples.

The aspect ratio and the color of the composition were evaluated purely visually, the aspect ratio being assessed as "clear", "cloudy" or inhomogeneous ("inh.").

For the determination of the tack-free time (skinning time), the compositions having room temperature were applied to cardboard in a layer thickness of approximately 3 mm and, in a standard climate ("SC"; 23±1° C., 50±5% relative humidity), in each case the time was determined that passed until no residue remained on a pipette made of LDPE when the surface of a composition was lightly tapped by way of the pipette.

The formation of bubbles was visually assessed based on the number ("many", "some", "none") of gas bubbles that developed during curing in the composition that was prepared for determining the skinning time.

The Shore A hardness was determined according to DIN 53505 on specimen that were cured for 7 days in a standard climate.

For the determination of the mechanical properties in the tensile test, films measuring approximately 3 mm thick were produced from the compositions by pouring the composition into a flat PTFE mold and curing it for 7 days in a standard climate. This yielded tack-free and elastic films. Dumbbells measuring 75 mm in length, having a web length of 30 mm and a web width of 4 mm, were punched out of the films, and some of these were tested in accordance with DIN EN 53504 for tensile strength, elongation at break and the modulus of elasticity (at 0.5 to 5.0% elongation) at a pulling speed of 200 mm/min. The remaining dumbbells were stored for 1 day at 100° C. in the circulating air oven, or for 10 days under "Cataplasma" (40° C. and 100% relative humidity), or for 10 days under "Cataplasma" and 1 day at 100° C., whereupon they were kept for one day in a standard climate and tested as described according to DIN EN 53504.

The results of these tests are listed in Table 2.

4200, from Bayer) and a catalyst according to Table 3 were homogeneously mixed in a centrifugal mixer (Speed-Mixer™ DAC 150, FlackTek Inc.) for 30 seconds at 3000 rpm for each example. A portion of the freshly prepared first component was then filled into an aluminum tube coated on the inside, the tube was hermetically sealed and stored for 7 days in a circulating air oven at 60° C.

TABLE 2

Properties of the two-component polyurethane compositions

| Example | 9 | 10 | V1 | V2 | V3 | V4 | V5 |
|---|---|---|---|---|---|---|---|
| Composition comprising freshly prepared first component: | | | | | | | |
| Aspect ratio | clear | clear | clear | clear | clear | inh. | clear |
| Color | colorless | colorless | colorless | colorless | colorless | yellow | colorless |
| Skinning time (min.) | 8 | 8 | 3 | 10 | 10 | 300 | 3 |
| Shore A hardness | 43 | 51 | 46 | 47 | 47 | 48 | 44 |
| Bubble formation | none | none | none | none | none | none | none |
| Tensile strength (MPa): | | | | | | | |
| 7 d/SC | 0.70 | 0.70 | 0.70 | 0.81 | 0.92 | 0.72 | 0.54 |
| + 10 d/Cataplasma | 0.73 | 0.83 | 0.65 | 0.82 | 0.79 | 0.71 | 0.79 |
| + 1 d/100° C. | 0.75 | 0.98 | 0.87 | 0.87 | 0.85 | 0.68 | 0.73 |
| + 10 d/Cataplasma + 1 d/100° C. | 0.85 | 0.86 | 0.79 | 0.77 | 0.93 | 0.67 | 0.73 |
| Elongation at break (%): | | | | | | | |
| 7 d/SC | 49 | 47 | 51 | 74 | 86 | 122 | 42 |
| + 10 d/Cataplasma | 59 | 60 | 50 | 75 | 66 | 122 | 73 |
| + 1 d/100° C. | 73 | 95 | 80 | 93 | 93 | 101 | 72 |
| + 10 d/Cataplasma + 1 d/100° C. | 82 | 78 | 72 | 81 | 95 | 93 | 74 |
| Mod. of elasticity (MPa): | | | | | | | |
| 7 d/SC | 1.81 | 2.00 | 1.72 | 1.61 | 1.68 | 0.74 | 1.46 |
| + 10 d/Cataplasma | 1.80 | 1.97 | 1.69 | 1.66 | 1.77 | 0.97 | 1.56 |
| + 1 d/100° C. | 1.48 | 1.82 | 1.72 | 1.50 | 1.64 | 1.03 | 1.49 |
| + 10 d/Cataplasma + 1 d/100° C. | 1.59 | 1.74 | 1.72 | 1.42 | 1.63 | 1.07 | 1.41 |
| Composition comprising stored first component: | | | | | | | |
| Aspect ratio | clear | clear | clear | clear | clear | inh. | clear |
| Color | colorless | colorless | colorless | colorless | colorless | deep-yellow | colorless |
| Skinning time (min.) | 15 | 12 | 20 | 82 | 205 | 12 | 45 |
| Shore A hardness | 47 | 47 | 44 | 46 | 47 | 48 | 45 |
| Bubble formation | none | none | none | some | none | none | some |

It is apparent from Table 2 that the two-component polyurethane compositions comprising the catalysts according to the invention represent clear, homogeneous mixtures, which have comparatively short skinning times, both before and after storage, and cure without bubbles, resulting in a material having comparatively high strength and good resistance.

Examples 11 to 12 and Comparison Examples V6 to V10

To produce the first component, a polyether triol (Voranol® CP 4755, from Dow), a polyether diol (Acclaim®

The remaining portion of the freshly prepared first component was mixed for each example in the described manner with a modified diphenylmethane diisocyanate (Desmodur® CD-L, from Bayer), which is liquid at room temperature, as the second component in accordance with Table 3 to form a polyurethane composition.

For each example, the first component, which had been stored for 7 days at 60° C., was likewise mixed with the second component in accordance with Table 3 in the same manner to form a polyurethane composition.

TABLE 3

Two-component polyurethane compositions (quantities in parts by weight).

| Example | 11 | 12 | V6 | V7 | V8 | V9 | V10 |
|---|---|---|---|---|---|---|---|
| First component: | | | | | | | |
| Voranol ® CP 4755 | 33.3 | 33.3 | 33.3 | 33.3 | 33.3 | 33.3 | 33.3 |
| Acclaim ® 4200 | 16.7 | 16.7 | 16.7 | 16.7 | 16.7 | 16.7 | 16.7 |
| Catalyst Bi1 | 0.022 | — | — | — | — | — | — |

TABLE 3-continued

Two-component polyurethane compositions (quantities in parts by weight).

| Example | 11 | 12 | V6 | V7 | V8 | V9 | V10 |
|---|---|---|---|---|---|---|---|
| Catalyst Bi3 | — | 0.030 | — | — | — | — | — |
| Catalyst Bi9 | — | — | 0.017 | — | — | — | — |
| Catalyst Bi11 | — | — | — | 0.014 | — | — | — |
| Catalyst Bi12 | — | — | — | — | 0.025 | — | — |
| Catalyst Bi14 | — | — | — | — | — | 0.040 | — |
| Coscat ® 83[a] | — | — | — | — | — | — | 0.020 |
| mmol-equiv./100 g[b] | 0.022 | 0.027 | 0.019 | 0.015 | 0.022 | 0.014 | 0.028 |
| Second component: | | | | | | | |
| Desmodur ® CD-L | 5.00 | 5.00 | 5.00 | 5.00 | 5.00 | 5.00 | 5.00 |

[a]Bismuth(III) tris(neodecanoate) in neodecanoic acid (16% Bi, from Erbslöh).
[b]mmol-equivalent bismuth atoms of the catalyst based on 100 g of the composition.

The polyurethane compositions were tested as described for Example 9 with respect to aspect ratio, tack-free time, bubble formation and the mechanical properties in a tensile test, in each case only for the composition comprising the freshly prepared first component.

The results of these tests are listed in Table 4.

filled into an aluminum tube coated on the inside, the tube was hermetically sealed and stored for 7 days in a circulating air oven at 60° C.

The remaining portion of the freshly prepared first component was mixed for each example in the manner described

TABLE 4

Properties of the two-component polyurethane compositions

| Example | 11 | 12 | V6 | V7 | V8 | V9 | V10 |
|---|---|---|---|---|---|---|---|
| Composition comprising freshly prepared first component: | | | | | | | |
| Aspect ratio | clear | clear | clear | clear | clear | clear | clear |
| Skinning time (min.) | 15 | 50 | 30 | 40 | 15 | 180 | 25 |
| Bubble formation | none | none | none | none | none | some | none |
| Tensile strength (MPa): | | | | | | | |
| 7 d/SC | 0.91 | 0.71 | 0.96 | 0.83 | 0.73 | 0.64 | 0.92 |
| + 10 d/Cataplasma | 0.81 | 0.80 | 0.74 | 0.81 | 0.81 | 0.65 | 0.92 |
| + 1 d/100° C. | 0.75 | 0.75 | 0.86 | 0.78 | 0.71 | 0.67 | 0.99 |
| + 10 d/Cataplasma + 1 d/100° C. | 0.83 | 0.81 | 0.74 | 0.81 | 0.68 | 0.72 | 0.98 |
| Elongation at break (%): | | | | | | | |
| 7 d/SC | 105 | 104 | 127 | 106 | 90 | 158 | 97 |
| + 10 d/Cataplasma | 95 | 103 | 94 | 122 | 105 | 151 | 98 |
| + 1 d/100° C. | 122 | 139 | 152 | 141 | 113 | 158 | 118 |
| + 10 d/Cataplasma + 1 d/100° C. | 121 | 127 | 104 | 121 | 97 | 187 | 103 |
| Mod. of elasticity (MPa): | | | | | | | |
| 7 d/SC | 1.48 | 1.04 | 1.30 | 1.37 | 1.23 | 0.54 | 1.67 |
| + 10 d/Cataplasma | 1.44 | 1.22 | 1.25 | 0.98 | 1.33 | 0.55 | 1.58 |
| + 1 d/100° C. | 1.12 | 0.97 | 0.78 | 1.00 | 1.03 | 0.75 | 1.46 |
| + 10 d/Cataplasma + 1 d/100° C. | 1.23 | 0.93 | 0.94 | 0.81 | 1.06 | 0.53 | 1.60 |
| Composition comprising stored first component: | | | | | | | |
| Aspect ratio | clear | clear | inh. | clear | clear | clear | clear |
| Skinning time (min.) | 25 | 55 | 120 | 270 | 35 | 210 | >240 |
| Bubble formation | none | none | none | none | none | some | many |

It is apparent from Table 4 that the two-component polyurethane compositions comprising the catalysts according to the invention represent clear, homogeneous mixtures, which have comparatively short skinning times and cure without bubbles, resulting in a material having comparatively high strength and good resistance.

Examples 13 to 19

As described for Example 9, in each case a polyether triol (Voranol® CP 4755, from Dow) and a catalyst were mixed in accordance with Table 5 to produce the first component. A portion of the freshly prepared first component was then for Example 9 with a modified diphenylmethane diisocyanate (Desmodur® CD-L, from Bayer), which is liquid at room temperature, as the second component in accordance with Table 5 to form a polyurethane composition.

For each example, the first component, which had been stored for 7 days at 60° C., was likewise mixed with the second component in accordance with Table 5 in the same manner to form a polyurethane composition.

The polyurethane compositions were tested as described for Example 9 with respect to aspect ratio, tack-free time, bubble formation and Shore A hardness.

The results of these tests are listed in Table 6.

TABLE 5

Two-component polyurethane compositions (quantities in parts by weight).

| Example | 13 | 14 | 15 | 16 | 17 | 18 | 19 |
|---|---|---|---|---|---|---|---|
| First component: | | | | | | | |
| Voranol ® CP 4755 | 30 | 30 | 30 | 30 | 30 | 30 | 30 |
| Catalyst Bi1 | 0.075 | — | — | — | — | — | — |
| Catalyst Bi2 | — | 0.055 | 0.025 | — | — | — | — |
| Catalyst Bi3 | — | — | — | 0.039 | 0.029 | — | — |
| Catalyst Bi4 | — | — | — | — | — | 0.027 | — |
| Catalyst Bi5 | — | — | — | — | — | — | 0.028 |
| mmol-equiv./100 g[a] | 0.127 | 0.074 | 0.033 | 0.059 | 0.044 | 0.031 | 0.030 |
| Second component: | | | | | | | |
| Desmodur ® CD-L | 3.10 | 3.10 | 3.10 | 3.10 | 3.10 | 3.10 | 3.10 |

[a]mmol-equivalent bismuth atoms of the catalyst based on 100 g of the composition.

TABLE 6

Properties of the two-component polyurethane compositions

| Example | 13 | 14 | 15 | 16 | 17 | 18 | 19 |
|---|---|---|---|---|---|---|---|
| Composition comprising freshly prepared first component: | | | | | | | |
| Aspect ratio | clear | clear | clear | clear | clear | clear | clear |
| Skinning time (min.) | 3 | 7 | 26 | 5 | 2 | 2 | 1 |
| Shore A hardness | 42 | 44 | 43 | 51 | 46 | 44 | 48 |
| Bubble formation | none | none | none | none | none | none | none |
| Composition comprising stored first component: | | | | | | | |
| Aspect ratio | clear | clear | clear | clear | clear | clear | clear |
| Skinning time (min.) | 11 | 15 | 55 | 7 | 5 | 6 | 3 |
| Shore A hardness | 45 | 43 | 47 | 50 | 49 | 48 | 48 |
| Bubble formation | none | none | none | none | none | none | none |

It is apparent from Table 6 that the two-component polyurethane compositions comprising the catalysts according to the invention represent clear, homogeneous mixtures, which have comparatively short skinning times, both before and after storage, and cure substantially without bubbles, resulting in a material having good Shore A hardness.

One-Component Polyurethane Compositions

Examples 20 to 23 and Comparison Examples V11 and V12

In a polypropylene beaker comprising a screw top, for each example the polyurethane polymer P1, the production of which is described hereafter, was mixed with a catalyst by way of a centrifugal mixer (SpeedMixer™ DAC 150, Flack-Tek Inc.; 1 min. at 2500 rpm) to form a homogeneous compound, and the compound thus obtained was immediately filled into an aluminum tube coated on the inside and then hermetically sealed.

The polyurethane polymer P1 was produced as follows:
1300 g polyoxypropylene diol (Acclaim® 4200 N, from Bayer; hydroxyl value 28.5 mg KOH/g), 2600 g polyoxypropylene polyoxyethylene trial (Caradol® MD34-02, from Shell; hydroxyl value 35.0 mg KOH/g), 600 g 4,4'-methylene diphenyl diisocyanate (4,4'-MDI; Desmodur® 44 MC L, from Bayer) and 500 g diisodecyl phthalate (DIDP; Palatinol® Z, from BASF) were reacted at 80° C., using known methods, to form an NCO-endcapped polyurethane polymer having a content of free isocyanate groups of 2.05% by weight.

The compositions thus obtained were tested for storage stability and curing speed.

As a measure of the storage stability, the change of the viscosity during storage in heat was determined. For this purpose, the compositions were stored in the sealed tube in the oven at 60° C. and the viscosity was measured at 20° C. a first time after 4 hours (="viscosity fresh") and a second time after 7 days (="viscosity w/storage"). The storage stability is derived from the increase, in percent, of the second viscosity value as compared to the first. For this purpose, the increase in viscosity in % is calculated according to the following formula:

[(viscosity after 7 d/viscosity after 4 h)−1]×100%.

As a measure of the curing speed, the tack-free time (skinning time) was determined, specifically for the compositions that were stored for 4 hours at 60° C. (="ST fresh") and for the compositions stored for 7 days at 60° C. (="ST w/storage"). For this purpose, the compositions having room temperature were applied to cardboard in a layer thickness of approximately 3 mm and, in a standard climate ("SC"; 23±1° C., 50±5% relative humidity), in each case the time was determined that passed until no residue remained on a pipette made of LDPE when the surface of a composition was lightly tapped by way of the pipette.

The results of these tests are listed in Table 7.

TABLE 7

One-component polyurethane compositions (quantities in parts by weight).

| Example | 20 | 21 | 22 | 23 | V11 | V12 |
|---|---|---|---|---|---|---|
| Polyurethane polymer P1 | 30 | 30 | 30 | 30 | 30 | 30 |
| Catalyst Example 6 | 0.63 | — | — | — | — | — |
| Catalyst Example 7 | — | 0.66 | 0.35 | — | — | — |
| Catalyst Example 8 | — | — | — | 0.59 | — | — |
| Coscat ® 83[a] | — | — | — | — | 0.37 | — |
| mmol-equiv.[b] | 0.9 | 0.9 | 0.5 | 0.9 | 0.9 | — |
| Viscosity fresh [Pa · s] | 71 | 92 | 91 | 88 | 108 | 68 |
| Viscosity w/ storage [Pa · s] | 101 | 174 | 133 | 131 | 169 | 97 |
| Increase in viscosity (%) | 42 | 90 | 45 | 49 | 57 | 42 |
| ST fresh (min.) | 50 | 51 | 104 | 47 | 50 | >360 |
| ST w/storage (min.) | 53 | 53 | 88 | 55 | 46 | >360 |

[a]Bismuth(III) tris(neodecanoate) in neodecanoic acid (16% Bi, from Erbslöh).
[b]mmol-equivalent bismuth atoms of the catalyst based on 100 g of the composition.

It is apparent from Table 7 that the one-component polyurethane compositions comprising the catalysts according to the invention exhibit comparatively good storage stability values and skinning times.

The invention claimed is:

1. A bismuth-containing catalyst, obtained by reacting at least one bismuth(III) salt or bismuth(III) complex with at least one 1,3-ketoamide with the formula (I),

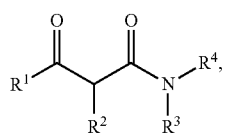

where $R^1$ and $R^2$ independently of one another are a hydrogen group, a monovalent saturated or unsaturated hydrocarbon group having 1 to 10 carbon atoms, or together are a bivalent alkylene group having 3 to 6 carbon atoms, and $R^3$ and $R^4$ independently of one another are a hydrogen group, a monovalent saturated hydrocarbon group, which optionally includes heteroatoms, having 1 to 12 carbon atoms, or together are a bivalent alkylene group, which optionally includes heteroatoms, having 3 to 6 carbon atoms.

2. The bismuth-containing catalyst according to claim 1, wherein the bismuth-containing catalyst has the formula $Bi(L)_x(Y)_{3-x}$, in which x is 1, 2 or 3, Y is a singly negative ligand, and L is a ligand with the formula (I).

3. The bismuth-containing catalyst according to claim 1, wherein $R^1$ is an alkyl group having 1 to 4 carbon atoms, a phenyl group, or together with $R^2$ is a bivalent alkylene group having 3 to 4 carbon atoms.

4. The bismuth-containing catalyst according to claim 1, wherein $R^2$ is a hydrogen group.

5. The bismuth-containing catalyst according to claim 1, wherein $R^3$ is a hydrogen group, an alkyl group having 1 to 8 carbon atoms, a cycloalkyl group having 5 to 6 carbon atoms, a hydroxyalkyl group having 1 to 4 carbon atoms, an alkyl ether group having 1 to 4 carbon atoms, or together with $R^4$ is a divalent alkylene group with the formula $-(CH_2)_n-X-(CH_2)_n-$ with X=O, NR, where R is a monovalent alkyl group having 1 to 4 carbon atoms, or S and n=2 to 6.

6. The bismuth-containing catalyst according to claim 1, wherein $R^4$ is a hydrogen group, an alkyl group having 1 to 8 carbon atoms, a cycloalkyl group having 5 to 6 carbon atoms, a hydroxyalkyl group having 1 to 4 carbon atoms or an alkyl ether group having 1 to 4 carbon atoms.

7. The bismuth-containing catalyst according to claim 1, wherein the stoichiometric ratio between the bismuth(III) salt or the bismuth(III) complex and the 1,3-ketoamide with the formula (I) ranges between approximately 1:0.5 and 1:20.

8. A method for producing the bismuth-containing catalyst according to claim 1, wherein at least one bismuth(III) salt or one bismuth(III) complex is reacted with at least one 1,3-ketoamide with the formula (I),

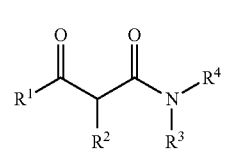

where $R^1$, $R^2$, $R^3$ and $R^4$ are as defined above.

9. The method according to claim 8, wherein a bismuth (III) carboxylate is used as the bismuth(III) salt or bismuth (III) complex.

10. A method comprising:
catalyzing curable compounds with the bismuth-containing catalyst according to claim 1.

11. A two-component polyurethane composition, comprising:
as a first component:
at least one polyol; and
at least one bismuth-containing catalyst according to claim 1; and
as a second component:
at least one polyisocyanate,
wherein the first and second components are stored in separate containers.

12. The two-component polyurethane composition according to claim 11, wherein the polyol is a polyether polyol and the polyisocyanate is a diisocyanate.

13. The two-component polyurethane composition according to claim 11, wherein the bismuth-containing catalyst accounts for 0.001 to 5 mmol-equivalent bismuth based on 100 g of the composition.

14. A one-component polyurethane composition, comprising at least one polyurethane prepolymer having isocyanate groups, produced from at least one polyisocyanate with at least one polyol, and at least one bismuth-containing catalyst according to claim 1.

15. A method comprising:
applying the two-component polyurethane composition according to claim 11 as a casting compound, sealant, adhesive, covering, coating, paint, subcoating, molding, or elastomer for building and industrial applications.

16. The bismuth-containing catalyst according to claim 1, wherein $R^1$ is butyl, $R^2$ is H, $R^3$ is butyl and $R^4$ is butyl.

* * * * *